United States Patent [19]

Meyer et al.

[11] 3,994,949

[45] Nov. 30, 1976

[54] PRODUCTION OF AROMATIC CYANIC ACID ESTERS

[75] Inventors: Karl-Heinrich Meyer; Claus Burkhardt; Ludwig Bottenbruch, all of Krefeld, Germany

[73] Assignee: Bayer Aktiengesellschaft, Germany

[22] Filed: Sept. 16, 1975

[21] Appl. No.: 613,755

[30] Foreign Application Priority Data

Sept. 26, 1974 Germany............................ 2446004

[52] U.S. Cl........................ 260/453 P; 260/453 AR
[51] Int. Cl.².......................................... C07C 122/00
[58] Field of Search.................. 260/453 P, 453 AR

[56] References Cited
UNITED STATES PATENTS

| | | | |
|---|---|---|---|
| 3,107,261 | 10/1963 | Gerber et al......................... | 260/453 |
| 3,553,244 | 1/1971 | Grigat et al......................... | 260/453 |

Primary Examiner—Elbert L. Roberts
Assistant Examiner—Dolph H. Torrence
Attorney, Agent, or Firm—Connolly and Hutz

[57] ABSTRACT

Aromatic cyanic acid esters are obtained by an improved process. Optionally substituted mononuclear phenols or polynuclear phenols optionally interrupted through bridge members such as

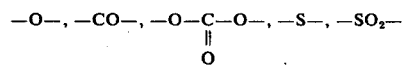

and/or divalent hydrocarbon bridges are condensated in form of an aqueous phenolate solution with cyanogen halide dissolved in organic solvents in the presence of catalytic quantities of a tertiary amine in a highly disperse system (two phase boundary reaction).

The cyanic acid esters obtained are highly pure and stable.

9 Claims, No Drawings

PRODUCTION OF AROMATIC CYANIC ACID ESTERS

It is known that aromatic cyanic acid esters can be obtained by reacting monophenols or polyphenols with cyanogen halide in the presence of organic or inorganic bases as acid binders. In one known process, described in German Auslegeschrift No. 1,195,764, the phenol together with an equivalent quantity of the cyanogen halide is reacted with an equivalent quantity of a tertiary amine in an inert organic medium (molar ratio 1 : 1 : 1).

In German Auslegeschrift No. 1,248,688, an inorganic base capable of phenolate formation under the reaction conditions, preferably an alkali hydroxide, is used instead of the tertiary amine.

Whereas in previously described reactions (Liebigs Ann. Chem. Vol. 287, page 319, and Ber. dtsch. chem. Ges. Vol. 28, page 2467) triazine derivatives were predominantly formed by way of the intermediate stage of imidocarbonic acid phenyl esters, the required cyanic acid esters are obtained by the processes described in the above mentioned patent specifications, but frequently in inadequate quality.

Impure cyanic acid esters are not very stable, since they readily form the aforementioned triazine derivatives, especially at elevated temperatures. Attempts to produce aromatic cyanic acid esters in the aqueous phase, for example by introducing cyanogen halide into an aqueous phenolate solution, generally lead to the imido carbonic acid phenyl ester stage.

It has now been found that highly pure, aromatic cyanic acid esters can be obtained by carrying out the reaction of phenolates with cyanogen halide as two phase boundary condensation in aqueous solution both in the presence of an organic solvent immiscible with water and in the presence of a catalytic quantity of a tertiary amine, and by taking suitable measures to produce a highly disperse system as the reaction medium in which the aqueous phenolate solution forms one phase whilst the solution of the cyanogen halide in an organic solvent forms the other phase.

In the context of the invention, aromatic cyanic acid esters are compounds corresponding to general formula (I) below $$R - (OCN)_n \qquad (I)$$

in which R represents an optionally substituted aromatic radical, for example, phenyl, phenylene or two or more such optionally substituted aromatic radicals (for example 2 to 10) which are attached to one another either directly or through bridge members for example, —O—, —CO—,

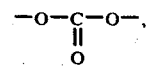

—S—, —SO$_2$— and/or divalent hydrocarbon bridges, for example lower alkylenes such as methylene, isopropylidene, cyclohexylidene, and $n$ can be a number from 1 to 5.

The aromatic radical may be substituted by one or more alkyl group with 1 to 9 carbon atoms, preferred with 1 to 4 carbon atoms; one or more alkoxy groups with 1 to 4 carbon atoms preferred with methoxy groups, one or more cycloalkyl groups with 5 to 10 carbon atoms, preferred with cyclohexyl groups, one or more halogene atoms, preferred fluorine and chlorine atoms, one or more nitro groups, one or more alkenyl groups with 2 to 6 carbon atoms, preferred allyl or vinyl groups, one or more alkyl carbonyl (R—CO—) groups with 1 to 4 carbon atoms in the alkyl group, preferred acetyl; one or more alkanoyl amino groups (R — CO — NH—) with 1 to 4 carbon atoms in the alkyl (R) group, preferred acetamino, one or more formyl groups, one or more alkoxycarbonyl groups (RO—CO—) with 1 to 12 carbon atoms in the alkoxy group preferred with 1 – 4 carbon atoms in the alkoxy group or phenoxycarbonyl groups.

The following are examples of cyanic acid esters corresponding to general formula (I) above: phenyl cyanate, 2-methyl phenyl cyanate, 3-methyl phenyl cyanate, 4-methyl phenyl cyanate, 2,6-dimethyl phenyl cyanate, 3,5-dimethyl phenyl cyanate, 2,4-diethyl phenyl cyanate, 2-tert.-butyl phenyl cyanate, nonyl phenyl cyanate, 4-cyclohexyl phenyl cyanate, 4-vinyl phenyl cyanate, 2-chlorophenyl cyanate, 3-chlorophenyl cyanate, 2,6-dichlorophenyl cyanate, 2-methyl-3-chlorophenyl cyanate, nitrophenyl cyanate, 4-nitro-2-ethyl phenyl cyanate, 3-methoxy phenyl cyanate, 2-methoxy-4-allyl phenyl cyanate, 4-methyl mercaptophenol cyanate, 3-trifluoro methyl phenyl cyanate, α-naphthyl cyanate, β-naphthyl cyanate, 4-cyanato diphenyl, 1,3-dicyanatobenzene, 1,4-dicyanatobenzene, 3,5-dicyanatotoluene, 1,3,5-tricyanatobenzene, 4-acetyl phenyl cyanate, 2-acetyl phenyl cyanate, 4-cyanatobenzaldehyde, 4-cyanatobenzoic acid methyl ester, 4-acetamidophenyl cyanate, 4-benzoyl phenyl cyanate, 4-cyanatobenzoic acid phenyl ester, 2,6-di-tert.-butyl phenyl cyanate, 5-cyanato quinoline, 4,4'-dicyanatodiphenyl, 2,2-bis-(4-cyanato phenyl)-propane, 2,2'-dicyanato-1,1'-dinaphthyl, 1,5-dicyanatoanthraquinone, 4,4'-dicyanatobenzophenone, 4,4'-dicyanato-3,3'-dimethoxy carbonyl diphenyl methane, 2,2-bis-(4-cyanato phenyl)-butane, 1,1-bis-(4-cyanato phenyl)-cyclohexane, 4,4'-dicyanatodiphenyl sulphone, 4,4'-dicyanato diphenyl ether, 4,4'-dicyanato diphenyl carbonate, 2,2-bis-(3,5-dimethyl-4-cyanato phenyl)propane, also

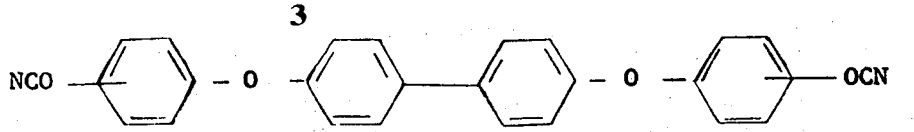

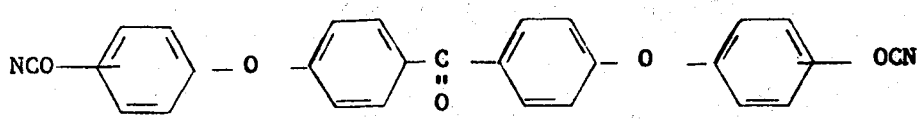

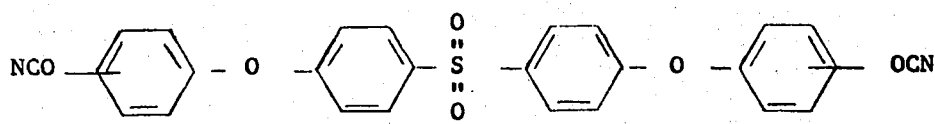

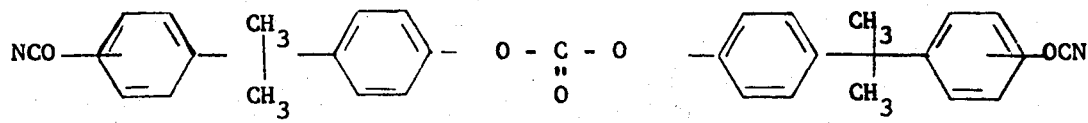

Phenols suitable for use in the preparation of the compounds of general formula (I) by the process according to the invention include monophenols and polyphenols which correspond to the general formula:

$$R — (OH)_m \qquad (II)$$

in which R represents an optionally substituted aromatic radical, for example, phenyl, phenylene or two or more such optionally substituted aromatic radicals (for example 2 to 10) which are attached to one another directly or through bridge members, for example —O—, —CO—,

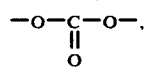

—S— —SO$_2$— and/or divalent hydrocarbon bridges for example lower alkylenes such as methylene, isopropylidene, cyclohexylidene, and m is an integer from 1 to 5.

The following are examples of phenols corresponding to the general formula (II): phenol, 2-methyl phenol, 3-methyl phenol, 4-methyl phenol, 2,6-dimethyl phenol, 3,5-dimethyl phenol, 2,4-diethyl phenol, 2-tert-butyl phenol, nonyl phenol, 4-cyclohexyl phenol, 4-vinyl phenol, 2-chlorophenol, 3-chlorophenol, 2,6-dichlorophenol, 2-methyl-3-chlorophenol, nitrophenol, 4-nitro-2-ethyl phenol, 3-methoxy phenol, 2-methoxy-4-allyl phenol, 4-methyl mercaptophenol, 3-trifluoromethyl phenol, α-naphthol, β-naphthol, 4-hydroxy diphenyl, resorcinol, hydroquinone, 3,5-dihydroxy toluene, 1,3,5-trihydroxy benzene, 4-acetyl phenol, 2-acetyl phenol, 4-hydroxy benzaldehyde, 4-hydroxy benzoic acid methyl ester, 4-acetaminophenol, 4-hydroxy benzophenone, 4-hydroxy benzoic acid phenyl ester, 2,6-di-tert.-butyl phenol, 5-hydroxy quinoline, 4,4'-dihydroxy diphenyl, 2,2-bis-(4-hydroxy phenyl)-propane, 2,2'-dihydroxy-1,1'-dinaphthyl, 1,5-dihydroxy anthraquinone, 4,4'-dihydroxy benzophenone, 4,4'-dihydroxy-3,3'-dimethoxy carbonyl diphenyl methane, 2,2-bis-(4-hydroxy phenyl)-butane, 1,1-bis-(4-hydroxy phenyl)cyclohexane, 4,4'-dihydroxy diphenyl sulphone, 4,4'-dihydroxydiphenyl ether, 4,4'-dihydroxy diphenyl carbonate, 2,2-bis(3,5-dimethyl-4-hydroxy phenyl)-propane, also

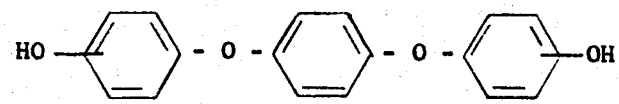

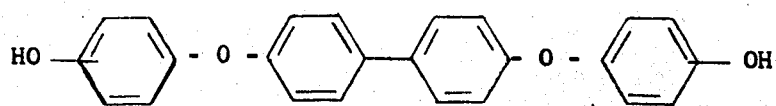

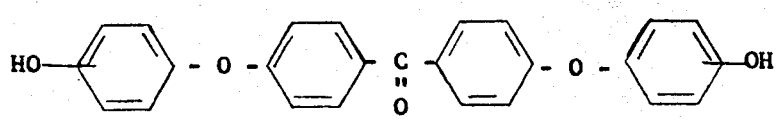

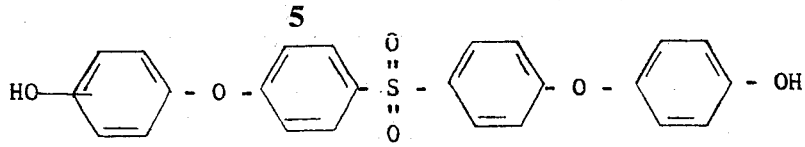

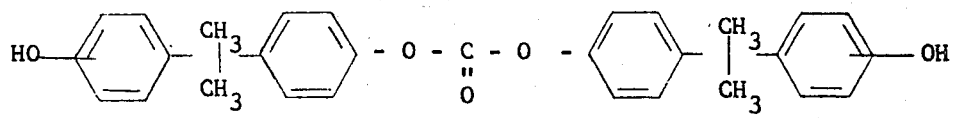

Particularly pure aromatic cyanic acid esters are obtained by the process according to the invention at temperatures below room temperature, preferably at temperatures in the range of 0° to 10° C, and at pH-values in the neutral to weakly acid range, preferably at pH-values in the range from about 5.5 to about 7.5. Under these conditions, the reaction takes place at a sufficiently high velocity. However, formation of the aromatic cyanic acid esters in accordance with the invention also takes place at higher temperatures and in alkaline medium.

It is particularly surprising that hydrolysis of the cyanogen halide by a secondary reaction is largely suppressed in the aqueous solution.

Highly disperse systems can be obtained for example by vigorously stirring (for example at 600 rpm) the mixture of an aqueous phenolate solution with, for example, aromatic hydrocarbons containing cyanogen halide, optionally in the presence of small quantities of surface-active substances.

Highly disperse systems can also be formed by pump-recirculating the aqueous phenolate solution together with the organic phase containing cyanogen halide at high speed through a pipe system. It is also known that highly disperse systems can be obtained by spraying one phase into the other. As any expert knows, nozzles, perforated plates, frits, etc., may be used for this purpose.

The phenols of formula II above are used in the form of aqueous phenolate solutions which are best prepared by dissolving a phenol in an alkali or alkaline earth liquor. It is best to use dilute solutions having a phenolate content which is normally less than 20% by weight. Particularly good results may be obtained with solutions having a phenolate content of from 3 to 10% by weight, preferably from 4 to 6% by weight.

Examples of suitable water-immiscible solvents are optionally substituted aromatic hydrocarbons, such as benzene, toluene, xylenes, ethyl benzene, chlorobenzene, dichlorobenzene, bromobenzene, nitrobenzene, tert.-butyl benzene, also optionally substituted aliphatic and cycloaliphatic hydrocarbons such as methylene chloride, chloroform, carbon tetrachloride, ethylene chloride, tetrachloroethane, trichloroethylene, ethyl bromide, n-propyl chloride, methylene bromide, nitromethane, n-hexane, cyclohexane, isooctane, cyclohexanone, cyclopentanone, 2-butanone, as well as ethers such as diethylether and diisopropyl ether. It can also be advantageous to use mixtures of the aforementioned water-immiscible solvents. Among these solvents, it is of particular advantage to use the aliphatic chlorinated hydrocarbons because they can be emulsified simply by gentle stirring with the aqueous phase and some of the cyanic acid esters formed are highly soluble therein, so that the reaction products can readily be separated.

In cases where it is intended to use surface-active substances, any ionic or non-ionic emulsifier that is active in neutral to weakly acid medium, for example polyglycol ethers, may be used for this purpose.

In the context of the invention, tertiary amines are compounds corresponding to the general formula (III)

in which $R_1$, $R_2$ and $R_3$ represent identical or different alkyl, aryl, cycloalkyl, alkaryl and aralkyl radicals having 1 to 25 carbon atoms which can be attached to one another to form rings. $R_1$, $R_2$ and $R_3$ preferably represent identical or different alkyl radicals having 1 to 12 carbon atoms hydroxyalkyl radicals having 2 to 6 carbon atoms, a cyclohexyl, phenyl, benzyl or diphenyl radical or together with nitrogen atom a pyridin radical or diazobicyclooctane.

The following are examples of suitable tertiary amines: trimethyl amine, triethyl amine, tri-n-butyl amine, triamyl amine, diethyl butyl amine, methyl dibutyl amine, tribenzyl amine, triethanolamine, dimethyl aniline, diethyl aniline, methyl ethyl butyl amine, tricyclohexyl amine, diphenyl methyl amine, diethyl cyclohexyl amine, pyridine, diazobicyclooctane, dodecyl dimethyl amine, etc.

The amines may be added both to the aqueous phenolate solution and also to the organic cyanogen halide solution. It may be advantageous to distribute the catalyst between both phases.

The quantity in which the tertiary amine is used generally amounts to from 0.01 to 10% by weight, based on the total quantity of the phenolic component. Particularly good results are obtained with additions of from 0.1 to 1% by weight.

The commercially readily available cyanogen chloride and cyanogen bromide may be used as the cyanogen halide. It is of advantage to use an excess of the cyanogen halide, for example quantities of from 5 to 100 mol percent, based on the phenolic OH-groups used, may be used.

The process according to the invention may be carried out by dispersing the aqueous phenolate solution in an excess of a solution consisting of the cyanogen halide in a solvent of the type just mentioned. It is also possible, however, initially to introduce only part of the cyanogen halide in the organic phase at the beginning of the reaction and to add the rest during the reaction either in liquid or gaseous form. In that case, however, an excess of aqueous phenolate solution should be avoided.

On completion of the reaction, the resulting dispersion of the aqueous inorganic salt solution and the solution of the aromatic cyanic acid ester formed in the indifferent solvent readily separates into an organic phase and an aqueous phase. The aromatic cyanic acid ester can be recovered from the organic phase after washing out with water and distilling off the solvent.

The process is particularly suitable for continuous working.

The invention is illustrated by but by no means limited to the following Examples. The percentages given in the Examples are by weight.

EXAMPLE 1

In a 1 liter capacity vessel equipped with a flatblade stirrer (10 cm² flat blade), solutions of 20 g of cyanogen chloride in 400 g batches of different organic solvents were cooled to +5° C, and 0.1 g of triethyl amine was added to each solution. This was followed by the dropwise addition of a solution cooled to 5° C of 20 g of bisphenol A, 7.3 g of NaOH and 500 ml of distilled water. This addition took place over a period of 30 minutes with stirring at different rotational speeds, while nitrogen was bubbled in as inert gas, the temperature being kept at 5° C by external cooling whilst the pH-value of the emulsion was kept at 5 – 6. On completion of the dropwise addition and stirring, the milky emulsion separated into two phases. The organic phase was washed with 3 × 200 ml of distilled water, followed by removal of the solvent at a temperature of <65° C/approx. 100 Torr. The residual melt began suddenly to crystallise.

Highly pure 2,2-bis-(4-cyanatophenyl)-propane melted at 82° C and had a refractive index $n_D^{90}$ of 1.5385. Deviations in the refractive indexes are a good indication of the presence of impurities. For example, values of 1.5390 indicate an impurity content of as much as 0.2%.

EXAMPLE 2

In a 1 liter vessel equipped with a flat-blade stirrer (10 cm² flat blade), solutions of 40 g of cyanogen chloride in 800 ml of methylene chloride were cooled to 5° C and 0.2 g of triethylamine added to each solution. Solutions cooled to 5° C of the phenols identified in Table 2 were then added dropwise with stirring at 600 rpm over a period of 30 minutes, during which time nitrogen was bubbled in as inert gas, the temperature being kept at 5° C by external cooling. The reaction mixtures were worked up in accordance with Example 1.

Table 2

| Test No. | Aqueous phenolate solution | Refractive index $n_D^{90}$ | % OCN found | theoretical | Yield % * | Remarks |
|---|---|---|---|---|---|---|
| 1 | 32.8g of phenol + 14.7g of NaOH + 1000g of H₂O | 1.5118 | 35.4 | 35.4 | 94.4 | light liquid |
| 2 | 64.2g of 2,2-bis-(3,5-dichloro-4-hydroxy phenyl)-propane + 14.7g of NaOH + 1000g of H₂O | decomp. <90° C | 19.9 | 20.2 | 99.5 | light crystals |
| 3 | 37g of 1,1-bis-(4-hydroxy phenyl)-cyclo hexane + 16.4g of NaOH + 1000g of H₂O | 1.5622 | 26.4 | 25.9 | 97.3 | yellowish melt |

* based on the phenol. component

EXAMPLE 3

In a water-cooled stirrer-equipped vessel with a lateral overflow, 840 g/h of a cyanogen chloride/methylene chloride solution (5% by weight of cyanogen chloride, 0.05% of triethyl amine) were continuously and intensively emulsified at 5° C with 1054 g/h of an aqueous sodium bisphenolate solution (3.8% of bisphenol A, 1.4% of NaOH, 0.05% of triethyl amine). In order to complete the reaction, the mixture was passed through another two water-cooled overflow vessels. The total residence time was about 15 minutes. The mixture was then collected in a glass vessel in which it separated into two liquid phases. The organic phase was worked up in accordance with Example 1. The 2,2-bis-(4-cyanatophenyl)propane obtained melted at 82° C and had a refractive index $n_D^{90}$ of 1.5385. Yield: 99%.

We claim:

1. A process for the production of an aromatic cyanic acid ester corresponding to the formula R — (OCN)$_n$ in which R represents one or more optionally substituted aromatic radicals which are attached to one another through at least one member selected from the group consisting of a direct linkage, Table 1

| Test No. | Solvent | Stirring speed rpm | Yield in % of the theoretical based on bisphenol A | Mp° C | Refractive index $n_D^{90}$ | Remarks |
|---|---|---|---|---|---|---|
| 1 | toluene | 1200 | 100 | 82° | 1.5385 | |
| 2 | toluene | 600 | 98.5 | 75–80° | 1.5412 | + 0.3 g of Erkantol BX |
| 3 | methylene chloride | 600 | 100 | 82° | 1.5385 | = emulsifier = di-n-butyl naphthlene-1-sulphonic acid |
| | 2,2-bis-(4-cyanatophenyl)-propane | | | 82°C | 1.5385 | |

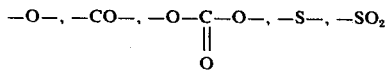

or a divalent hydrocarbon bridge and n is a number from 1 to 5, said process comprising reacting a corresponding aqueous phenolate solution having a phenolate content less than 20% by weight with cyanogen halide dissolved in an organic, water-immiscible solvent in the presence of a catalytic amount of a tertiary amine in a highly disperse system as a two phase boundary reaction.

2. The process as claimed in claim 1, wherein the reaction is carried out at 0° to 10° C in a neutral or weakly acid pH-range.

3. The process as claimed in claim 1, wherein an aqueous phenolate solution containing from 3 to 10% by weight of phenolate is used.

4. The process as claimed in claim 1, wherein the reaction is carried out in the presence of an excess of cyanogen halide.

5. The process as claimed in claim 1, wherein the reaction is carried out in the presence of 0.01 to 10% by weight of a tertiary amine, based on the total quantity of the phenolic component.

6. The process as claimed in claim 1, wherein said phenolate is 2,2-bis-(4-hydroxyphenyl)propane.

7. The process as claimed in claim 1, wherein said phenolate is phenol.

8. The process as claimed in claim 1, wherein said phenolate is 2,2-bis-(3,5-dichloro-4-hydroxyphenyl)-propane.

9. The process as claimed in claim 1, wherein said phenolate is 1,1-bis-(4-hydroxyphenyl)cyclohexane.

* * * * *